United States Patent [19]
Kuehn et al.

[11] 3,992,942
[45] Nov. 23, 1976

[54] APPARATUS FOR DETERMINING WET BULB GLOBE TEMPERATURE

[75] Inventors: Lorne A. Kuehn, Downsview; Lloyd E. McHattie, Willowdale, both of Canada

[73] Assignee: Her Majesty the Queen in right of Canada, as represented by the Minister of National Defence, Ottawa, Canada

[22] Filed: Mar. 11, 1974

[21] Appl. No.: 449,855

[30] Foreign Application Priority Data

Mar. 30, 1973 Canada .................. 167561

[52] U.S. Cl. .................. 73/336.5; 73/338; 73/339 C
[51] Int. Cl.² .................. G01W 1/17
[58] Field of Search .................. 73/336, 336.5, 338, 73/339 C

[56] References Cited
UNITED STATES PATENTS

| | | | |
|---|---|---|---|
| 2,154,927 | 4/1939 | Yaglou | 73/339 C X |
| 2,256,127 | 9/1941 | Smith | 73/336.5 X |
| 2,398,333 | 4/1946 | Shoemaker | 73/339 C X |
| 3,095,742 | 7/1963 | Pelishek | 73/336 |
| 3,124,002 | 3/1964 | Pierson et al. | 73/336 |
| 3,531,991 | 10/1970 | Strong et al. | 73/355 R |
| 3,603,135 | 9/1971 | Kawaguchi | 73/338 X |
| 3,771,364 | 11/1973 | Worthington | 73/336 |
| 3,817,102 | 6/1974 | Shea | 73/338 |
| 3,855,863 | 12/1974 | Kuehn et al. | 73/339 C |

FOREIGN PATENTS OR APPLICATIONS

Ad. 45,139    6/1935    France .................. 73/339 C

*Primary Examiner*—Richard C. Queisser
*Assistant Examiner*—Frederick Shoon
*Attorney, Agent, or Firm*—R. William Wray & Associates

[57] ABSTRACT

Apparatus for determining the wet bulb globe temperature (WBGT) index of the surroundings constructed from a copper globe having a blackened exterior surface and provided with a fabric cover, which may entirely surround the globe or may be in strips or strands extending over the surface of the globe, with a source of water to maintain the fabric cover at least partially wet. A temperature sensing device, which may conveniently be a glass thermometer, as its sensing portion located at the center of the globe whereby a measurement of the wet bulb globe index of the surroundings can be obtained.

22 Claims, 6 Drawing Figures

APPARATUS FOR DETERMINING WET BULB GLOBE TEMPERATURE

BACKGROUND OF THE INVENTION

This invention relates to apparatus for determining the wet bulb globe temperature (WBGT) index of the surroundings.

As is well known, the wet bulb globe temperature is a practical index of heat stress on living organisms, notably human beings, in hot environments. It is a composite measure of the four factors affecting thermal comfort in man, namely, air temperature, relative humidity, air movement and thermal radiation level. The wet bulb globe temperature is calculated from the formula:

| (1) | WBGT | = | 0.7 WB + 0.2 GT + 0.1 DB |
|---|---|---|---|
| where | WBGT | = | wet bulb globe temperature index |
| | WB | = | natural wet bulb temperature |
| | GT | = | 6 inch black globe temperature |
| and | DB | = | shaded dry bulb temperature. |

The above temperatures may be in ° C. or ° F. The globe temperature is a composite measure of thermal radiation and convection and conduction exchanges with the environment and is measured with a temperature sensor positioned at the center of the inside of a standard 6 inch diameter metallic globe with a blackened surface.

At present the most common method of measuring the wet bulb globe temperature (hereinafter referred to as the WBGT) of a particular environment is by measuring the three individual temperatures, the wet bulb temperature, the globe temperature and the dry bulb temperature and substituting these measurements into the above formula to determine the WBGT value. Each individual determination of a WBGT with this method requires approximately five minutes. None of the three temperature measurements are made at exactly the same time so that the WBGT value derived does not represent an instantaneous value applicable to the particular environment. Additionally, errors can be made in the individual temperature measurements or in the calculations itself, thus requiring individual checking and verification of these steps. Previously proposed WBGT meters incorporate three sensors, a dry bulb temperature sensor, a wet bulb temperature sensor, and a globe temperature sensor. The globe temperature sensor is usually the standard 6 inch diameter globe which has a time of response to a temperature change in the order of 20 minutes, so that, in environments of rapidly changing heat stress, these instruments do not measure the instantaneous WBGT value.

It is an object of the present invention to a simplified apparatus for determining the wet bulb globe temperature (WBGT) index of the surroundings in which only one temperature sensor is used.

Accordingly, the present invention provides a wet bulb globe temperature measuring instrument for determining the wet bulb globe temperature index of the surrounding comprising a globe member of metallic material provided with a fabric cover jacket over at least a part of its external surface, means for maintaining said cover jacket at least partially wet when exposed to the environment, and a temperature sensing device located within said globe member to provide a measurement of the wet bulb globe temperature index of the surroundings.

DRAWINGS

Some embodiments of the present invention will now be described by way of example with reference to the accompanying drawings in which:

FIG. 1 is a diagrammatic representation of a wet bulb globe temperature measuring instrument according to one embodiment of the invention and FIG. 2 shows graphically the results of regression analysis of performance of various models of a single thermometer WBGT index instrument in the open atmosphere.

FIG. 3 is a diagrammatic representation of an instrument similar to FIG. 1 but wherein two diametrically opposite strands are maintained in a dry condition, FIG. 4 is a diagrammatic representation of an instrument wherein each dry strand is separated from the next by three wet strands, FIG. 5 is a diagrammatic representation of a wet bulb globe temperature measuring instrument in which a nylon jacket entirely covers the sphere, and FIG. 6 illustrates the use of an electrical or electronic sensor.

DETAILED DESCRIPTION

Figure 1:
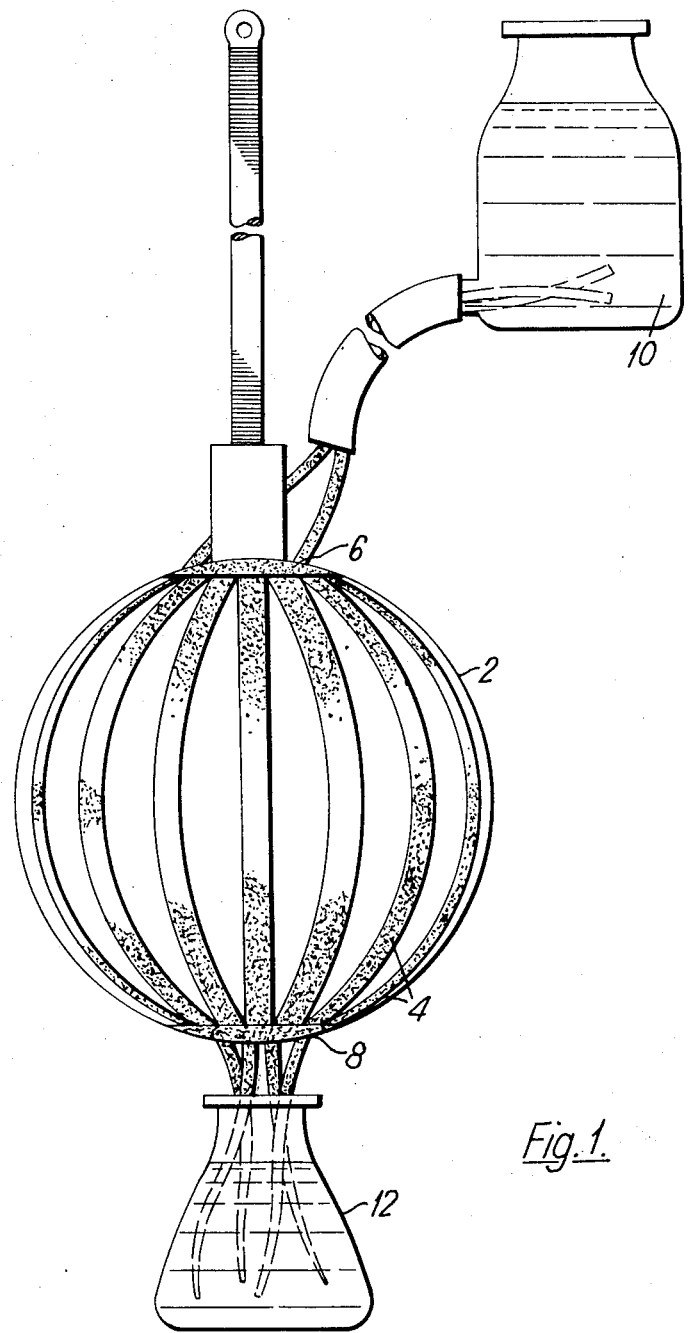

The arrangement illustrated in FIG. 1 is of a wetted strand version of the single thermometer WBGT index meter or instrument. It will be appreciated that several experimental models of a single-bulb WBGT index meter were constructed for study. The globe in each case was a hollow copper sphere 4 inches in diameter spun from sheet copper with a thickness of 0.022 in. It was painted with two coats of flat black paint (which has an emissivity of approximately 0.95). The size and emissivity of the sphere were in accordance with a semi-empirical formula relating these characteristics to the animal for which the globe is an analogue in this case man. The temperature at the center of the globe was measured with a Fahrenheit mercury thermometer which was inserted vertically into the globe. In all models, the globe was covered fully or partially with a porous fabric jacket from which porous wicks descended to a small-mouthed water reservoir positioned below the globe, the fabric jacket being tied at the bottom of the globe with the porous wicks which were of cotton and ¼ inch wide. It was soon found that these wicks did not pass enough water by capillary action to ensure a uniform wetting of the fabric on the globe, and in most of the models a second reservoir was necessary, positioned above the globe and removed slightly from it, so that as little radiation shadow as possible fell on the globe's surface. A vinyl tube containing two wicks connected the upper reservoir to the upper regions of the fabric on the globe. The rate of flow of water from this upper reservoir was such that the porous fabric on the globe had water passing through it to the bottom reservoir. This was accomplished by restricting the flow of water through the vinyl tube with a Hoffman screw clamp. The globe was then surrounded by a 'film' of water. Distilled water was used in all models to cool the globe so that the fabric would remain clean and retain its characteristics over a long period of time.

One embodiment is shown in FIG. 1 and is a wetted strand version. A globe 2 was partially covered by a fabric jacket 4 made of 16 pieces of soft cotton tape 0.25 in wide that were uniformly spaced in a vertical arrangement around the globe and joined at the poles 6 and 8. The cotton tape was woven with 15 warp (or lengthwise) yarns, and 13 filling yarns per in. Its weight was 260 yards per lb. The surface area of the globe 2 covered by the fabric jacket 4 was approximately 42% of the total surface area. To ensure uniform wetting of the strands, an upper reservoir 10 of distilled water and a lower reservoir 12 of distilled water were provided, as shown.

Figure 3:
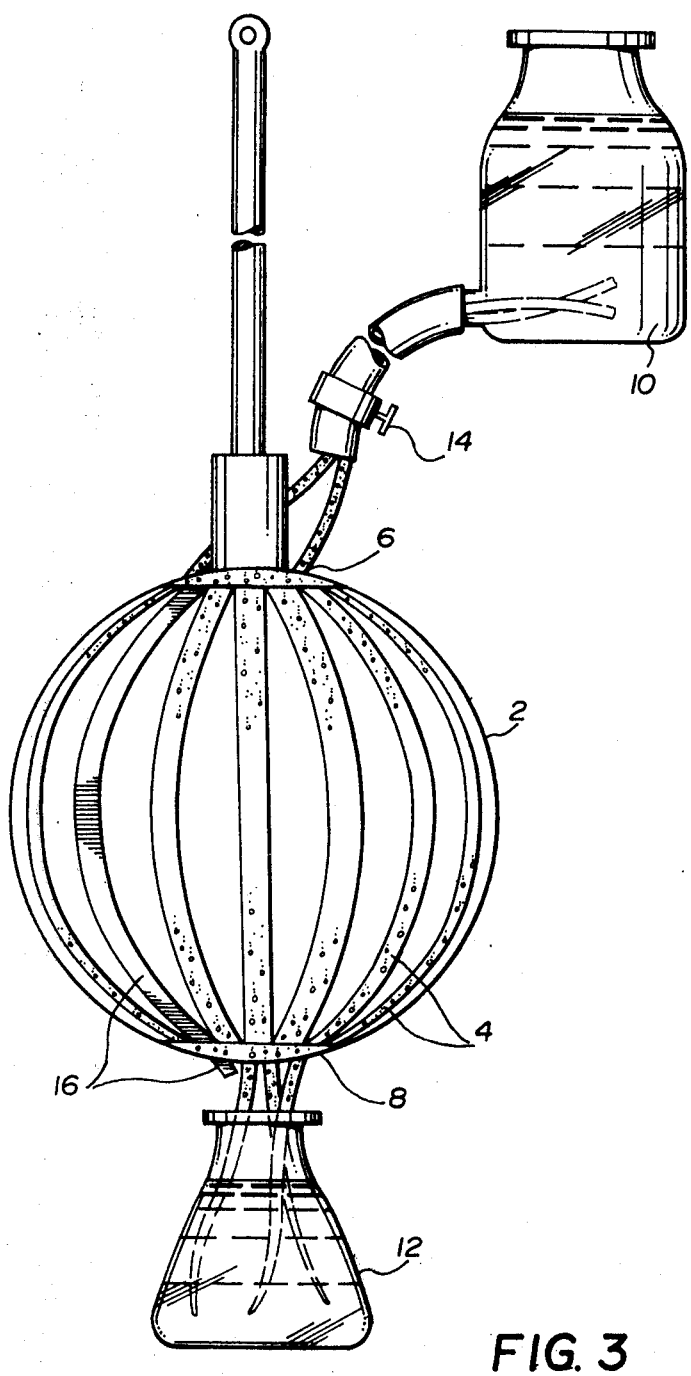
Figure 4:
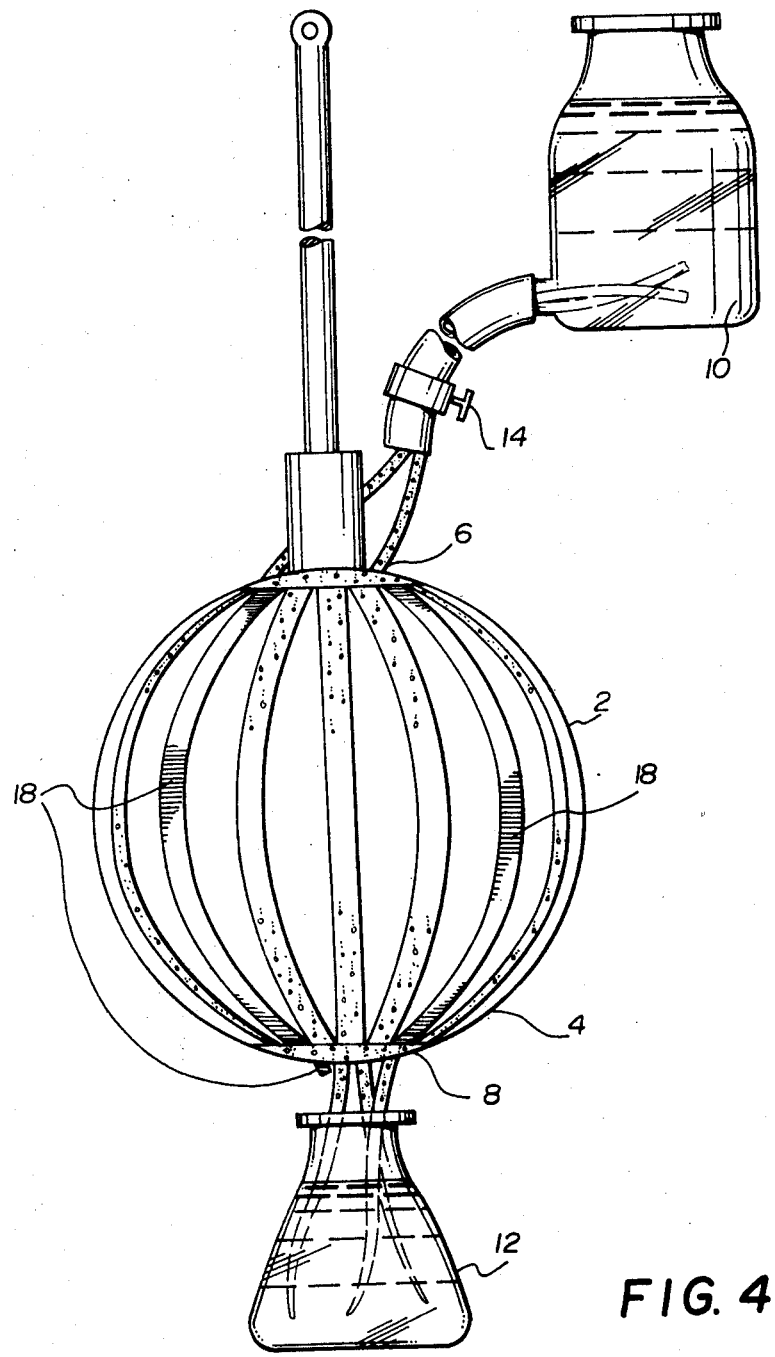

The constructional arrangement as shown in FIG. 1 was operated in a number of satisfactory ways.

i. in the first version of FIG. 1 all 16 strands were either totally wet or at least partially wet;

ii. in the second version of FIG. 1, as shown in FIG. 3, 16 strands making up the jacket 4 were again provided but this time, two strands, such as 16, which were diametrically opposed to each other, were arranged to remain dry during operation of the measuring instrument. A representative control means 14 is shown for controlling the supply of water to the jacket 4.

iii. in a third version (FIG. 4) 16 strands were again provided around the blackened copper globe member 2 but three wet strands were interposed between each pair of dry strands, i.e., the four dry strands, such as 18, were separated from each other by three wet strands.

It will be appreciated that a dry strand was one that was severed from the others so that no water could pass through it.

In versions (ii) and (iii) the orientation of wet and dry strands was such that an asymmetric moisture pattern was present to point sources of radiation, such as in the next two embodiments described below, however, the magnitude of this effect on the reading of the thermometer was apparently not large enough to be significant.

Wetted Cotton Cover Model

The globe 2 was covered with a close fitting double-layered jacket 4 of cotton fabric that entirely covered the surface. A 1 × 1 rib knit cotton fabric, 6 oz. yd.$^{-2}$ with 24 wales and 32 courses per inch was used in the form of a tube that was 3.0 inches wide when flat. The jacket 4 consisted of a circular cylinder of cotton fabric which was passed through a stainless-steel ring ½ inch in diameter and then doubled back on itself to produce two layers. The ring was positioned at the top of the globe and the thermometer was inserted through it. The wicks from the upper reservoir 10 were sewn into the jacket 4 near the ring and the jacket was tied at the bottom of the globe with the wicks from the lower reservoir 12. Three versions of this design were constructed: (a) totally wetted black cotton jacket with upper and lower reservoirs, (b) totally wetted white cotton jacket with upper and lower reservoirs, and (c) partially wetted black cotton jacket with lower reservoir only.

Wetted Nylon Cover Model

Figure 5:
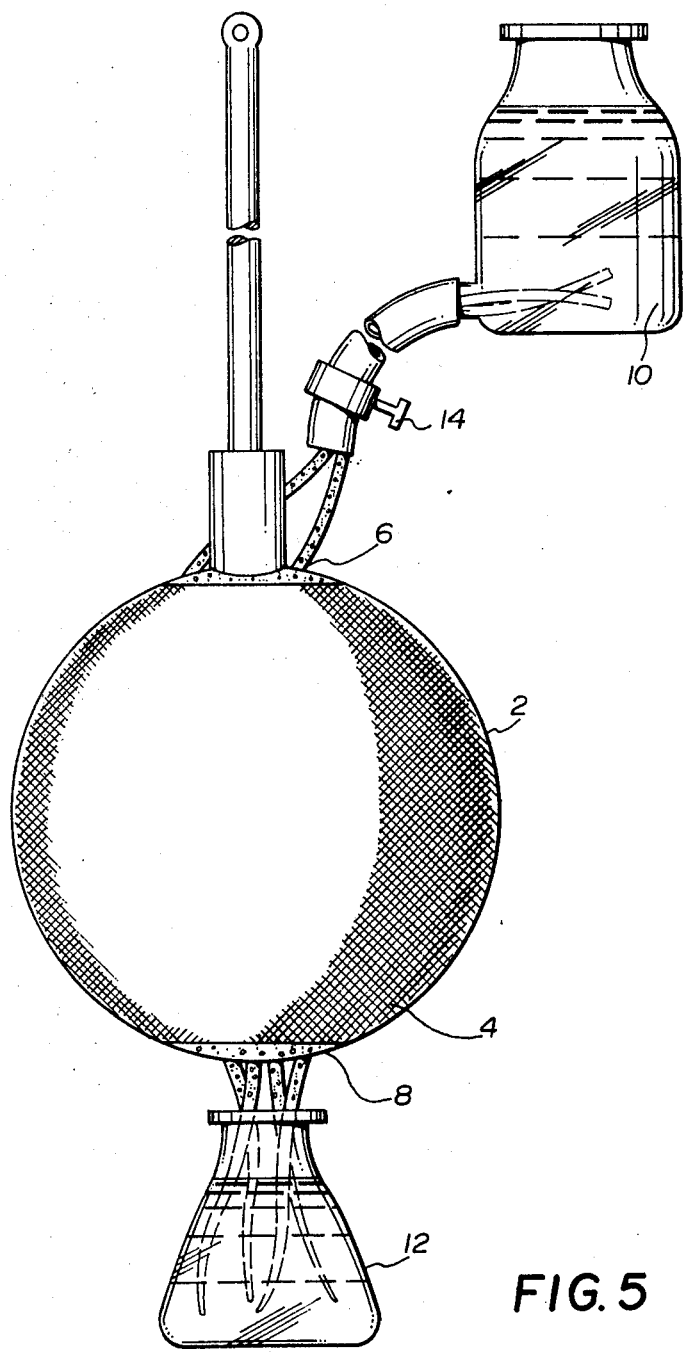

The globe 2 was covered with a close-fitting double layered jacket 4 in the same manner as were the cotton covered versions, as shown in FIG. 5. A black 4 × 2 rib knit fabric, 8 oz. yd.$^{-2}$, with 34 wales per in and 28 courses per in, was prepared in the form of a tube that was 2.5 in wide when flat, and formed into a jacket by passing through a ½-inch stainless steel ring as described above. This version employed both upper and lower water reservoirs.

Several calibrations under laboratory conditions were performed to determine the response of the wetted strand versions. In radiation tests the wetted spheres were set up with their centers at a distance of 3 ft from a large gas flame in a conditioned room (maintained at 70° F., 65% relative humidity with air movement in the range 0 – 20 m min$^{-1}$). An electronic WBGT meter that was accurate to within 0.5° F. was placed at the same distance from the burner to measure directly the WBGT index in these experiments. Wetted sphere thermometer readings were obtained for various intensities of the gas flame, and the influence of the number of wetted strands on the thermometer readings was determined in the WBGT range 65° – 85° F. The fewer the wet strands, the greater the difference between the readings of the wetted sphere and the control WBGT meter. The closest match was obtained with a globe that had 16 wetted strands.

The dependence of the response of the globes to variation of humidity was determined from a series of humidity tests in a climatic chamber in which the environment of the globe was maintained at a constant (air) temperature (with an air movement in the range 3 – 55 m min$^{-1}$) while the humidity was varied. At each of a series of air temperatures between 60° and 100° F. the relative humidity was maintained at various levels in the range between 25 and 90%. Again, several globes with different numbers of wetted strands were examined, but best agreement with the control WBGT index value was obtained with a globe with 14 wetted and two dry strands. Low humidity conditions (below 50% relative humidity for air temperatures in the range 50° – 100° F.) resulted in poor agreement between the wetted sphere and the control meter.

All the spheres were exposed for several hundred hours to the sun's radiation in the open atmosphere above a pea gravel surface with an air movement ranging from still air to that of a gentle breeze, and their readings taken every 2 or 3 hours were compared with those of an electronic control WBGT index meter in the range 60° – 90° F. The environmental extremes in which these tests were conducted were as follows: DB: 60.3° – 100.0° F; WB: 52.7° – 80.0° F.; GT: 61.9° – 110.0° F.; relative humidity: 20 – 80%; WBGT: 56.2° – 90.0° F. The results of these tests were then subjected to linear regression analysis and equations of the 'best fitting' straight lines were obtained in the form $$WBGT_{ws} = mWBGT_c + b \qquad (2)$$

where $WBGT_{ws}$ is the wetted sphere response, $WBGT_c$ the electronic WBGT index meter response, $m$ is a constant, slope of 'best fitting' line, and $b$ a constant, intercept of $WBGT_{ws}$ on the line $WBGT_c=0$. Table 1 shows the results of the computation and FIG. 2 depicts the 'best fitting' lines for all of the spheres tested.

Figure 2:
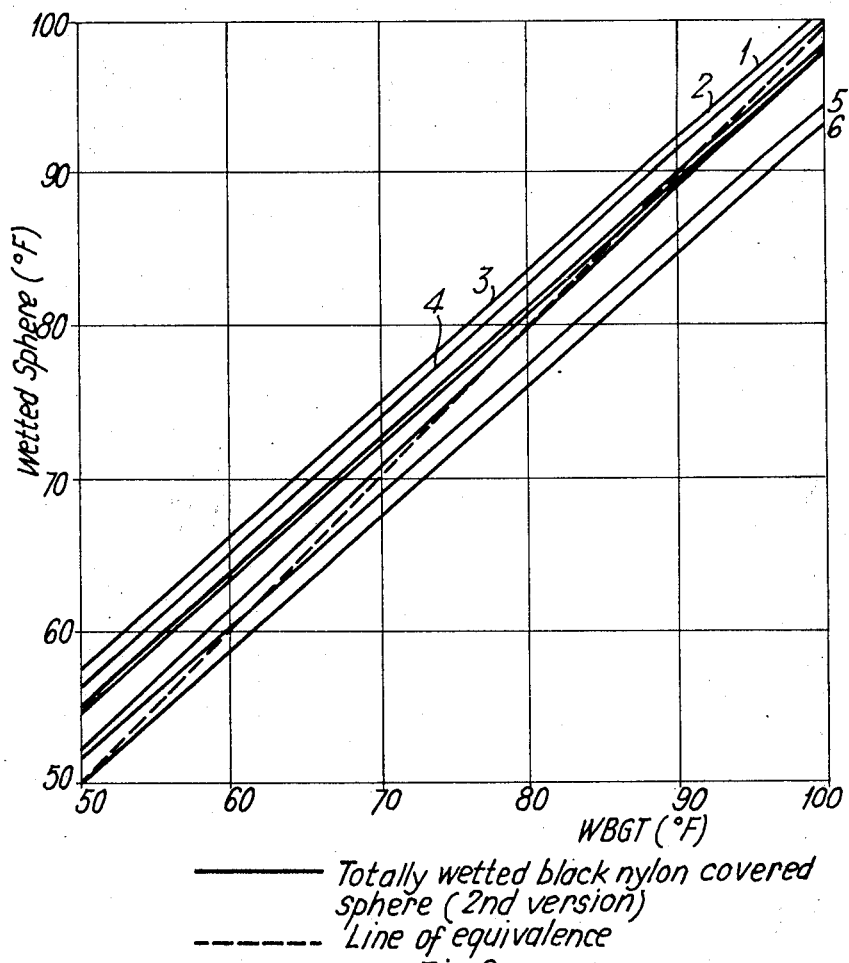

It is seen from the Table 1 and also from FIG. 2 that the totally wetted double-layered black nylon model approximates the control WBGT index meter in the range 60° – 90° F. Two of the other designs offer promise. These are two of the wetted strand versions — the basic model with 16 wet strands and the same model with 14 wet and two dry strands.

It will be seen that FIG. 2 gives the results of regression analysis of performance of various models of the single thermometer WBGT index meter in the open atmosphere (in sunshine above a pea gravel surface with low wind movement): 1, partially wetted block cotton covered sphere; 2, 16 strand — four dry; 3, 16 strand — two dry; 4, 16 strand — all wet; 5, totally wetted black cotton covered sphere; 6, totally wetted white cotton covered sphere. The unnumbered solid line is the totally wetted black nylon covered sphere.

As expected from the results of the humidity experiments on the wetted strand models, good agreement (within 1° F) of the above three best designs with the control WBGT index meter was obtained only for certain conditions of humidity (greater than 50% relative humidity) and air temperatures in the range 60° – 100° F. In relation to human performance, however, these are the conditions in which a knowledge of the WBGT index is required most critically.

Table 1

Linear regression analysis of wetted sphere performance in natural environments

| Type of wetted sphere | Slope m | Intercept b (° F.) |
|---|---|---|
| Wetted strand model, 16 wet strands | 0.874 | 11.0 |
| Wetted strand model, 14 wet and 2 dry strands | 0.874 | 11.3 |
| Wetted strand model, 12 wet and 4 dry strands | 0.885 | 12.1 |
| Totally wetted black cotton covered sphere | 0.868 | 8.24 |
| Totally wetted white cotton covered sphere | 0.870 | 6.54 |
| Partially wetted black cotton covered sphere | 0.869 | 14.2 |
| Totally wetted black nylon covered sphere | 0.937 | 5.19 |

These instruments require approximately 22 minutes to respond to a sudden change in conditions. Although this time is no longer than that required for an electronic WBGT index meter to respond fully to the same impulse (13 minutes), it compares reasonably well with the time required for full response of 4 inch and 6 inch diameter black globe thermometers (16 and 18 minutes).

The prime advantages of the described embodiments appear to be that they use only one temperature sensor and that they provide the value of the WBGT index in one reading; furthermore, they have no electrical power requirements. Experiments have shown, however, that on a very hot dry day approximately 100 cm³ of distilled water will be required for the instruments' daily water loss. It has also been established that the rate of water flow through the covering fabrics is not important provided that saturation with water is maintained. However, it is necessary to use fabrics of the same characteristics and orientation on the specified globe as indicated above in order to guarantee the same degree of correlation of the meter with the WBGT of the environment.

It will be appreciated that the double nylon covering referred to above is wet to the touch all over and the appearance is appreciably different when wet so that one could tell by looking at it whether it was properly wetted but the outer layers were not completely sopping wet. The flow of water was adjusted by the clip control on the tube from the upper reservoir so that the flow of water was just enough to wet the inside surface of the nylon. The outer layer was not completely wet, otherwise the temperature reading obtained in the shade would be the true wet bulb temperature. What is required is a temperature which is not quite as low as that but corresponds to the wet bulb globe temperature index. The control was adjusted so that small drops of water formed very slowly on the bottom of the wick so that you could just detect that they were growing — it was then thought that the flow of water was mainly down between the inner layer and the copper globe.

From the above, it will be seen that there were constructed several designs of a one-bulb WBGT index instrument or meter. The most successful of these were: (1) a totally wetted black nylon covered sphere and (2) a 16 strand sphere having 14 strands wet. Of these two, it appears that the first one is the most suitable for use in outdoor environments since the Table 1 and FIG. 2 indicate that it most closely follows the control WBGT meter response in the region 60° – 90° F. WBGT. The other one most closely matches the control WBGT meter response in situations where the mean radiation temperature of the environment equals air temperature, i.e., in situations where humidity alone is the determining heat stress factor, such as mines or enclosed spaces.

The instruments described apparently offer the simplicity and economy of standard mercury-in-glass thermometers but share also their fragility and relatively slow response in air. Nevertheless, if used with reasonable care and within the limits indicated, they are apparently capable of yielding satisfactory results.

Figure 6:
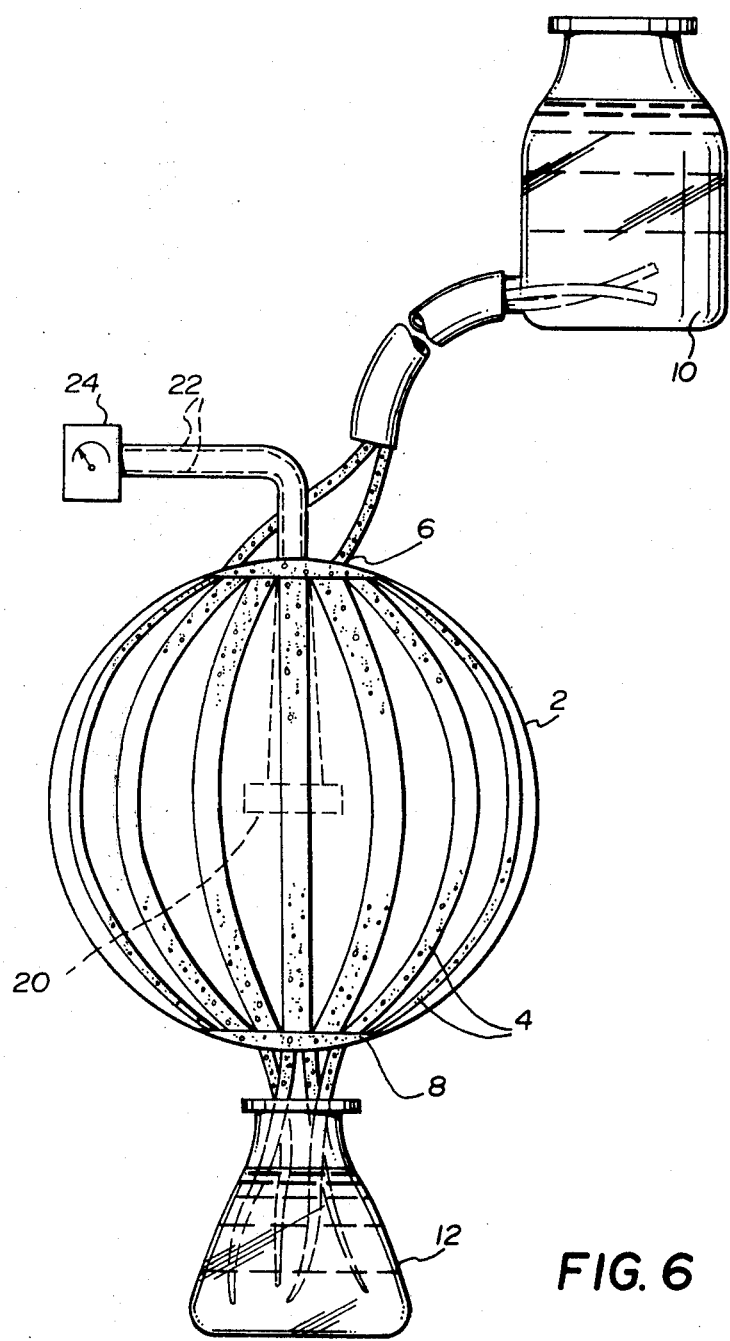

In the above description, the use of a mercury-in-glass thermometer has been described. It will, however, be appreciated that the invention is not restricted thereto, but any suitable temperature indicating device might conveniently be provided at the center of the globe. For example, a temperature sensor 20, which may be electrical or electronic, could be substituted as the measuring thermometer instrument, as shown in FIG. 6, connected through connections 22 to a temperature indicating device 24.

We claim:

1. A wet bulb globe temperature index measuring instrument for determining the wet bulb globe temperature index of the surroundings comprising a 4-inch diameter metallic sphere with a black external surface and an emissivity of substantially 0.95 provided with a fabric cover jacket over at least a part of its external surface, means for maintaining said cover jacket at least partially wet when exposed to the environment, and a temperature sensing device located substantially at the center of said globe sphere to determine the temperature at said center and to provide a measurement of the wet bulb globe temperature index of the surroundings.

2. A temperature measuring instrument according to claim 1 wherein said metallic sphere is a hollow copper sphere, and said fabric cover jacket is a close-fitting double-layered jacket of black knitted nylon fabric entirely covering the external surface of the said sphere.

3. A temperature measuring instrument according to claim 1 wherein said metallic sphere is a hollow copper sphere, and said fabric cover jacket comprises 16 strands of soft cotton tape uniformly spaced around the globe in a vertical arrangement, the strands covering approximately 42% of the total surface area of the sphere.

4. A temperature measuring instrument according to claim 3 wherein all 16 strands are maintained in a wet condition.

5. A temperature measuring instrument according to claim 3 wherein two of said strands diametrically opposed to each other are maintained in a dry condition with the remaining strands wet.

6. A temperature measuring instrument according to claim 3 wherein four of said strands are maintained in a dry condition, each dry strand being separated from the next by three wet strands.

7. A temperature measuring instrument according to claim 1 wherein said metallic sphere is a hollow copper sphere and said fabric cover jacket is a close-fitting double-layered jacket of cotton fabric covering the external surface of said sphere.

8. A temperature measuring instrument according to claim 2, wherein an upper reservoir of distilled water is provided having wicks extending to the top of said fabric cover jacket to maintain it partially wet, control means being provided to control the supply of water to said jacket, and wherein wicks are provided from the bottom of said jacket extending into a lower reservoir.

9. A temperature measuring instrument according to claim 3, wherein an upper reservoir of distilled water is provided having wicks extending to the top of said fabric cover jacket to maintain it partially wet, control means being provided to control the supply of water to said jacket, and wherein wicks are provided from the bottom of said jacket extending into a lower reservoir.

10. A temperature measuring instrument according to claim 4 wherein an upper reservoir of distilled water is provided having wicks extending to the top of said fabric cover jacket to maintain it partially wet, control means being provided to control the supply of water to said jacket, and wherein wicks are provided from the bottom of said jacket extending into a lower reservoir.

11. A temperature measuring instrument according to claim 5, wherein an upper reservoir of distilled water is provided having wicks extending to the top of said fabric cover jacket to maintain it partially wet, control means being provided to control the supply of water to said jacket, and wherein wicks are provided from the bottom of said jacket extending into a lower reservoir.

12. A temperature measuring instrument according to claim 6, wherein an upper reservoir of distilled water is provided having wicks extending to the top of said fabric cover jacket to maintain it partially wet, control means being provided to control the supply of water to said jacket, and wherein wicks are provided from the bottom of said jacket extending into a lower reservoir.

13. A temperature measuring instrument according to claim 7, wherein an upper reservoir of distilled water is provided having wicks extending to the top of said fabric cover jacket to maintain it partially wet, control means being provided to control the supply of water to said jacket, and wherein wicks are provided from the bottom of said jacket extending into a lower reservoir.

14. A temperature measuring instrument according to claim 2, wherein said temperature sensing device is a mercury-in-glass thermometer having its bulb located within said metallic sphere and its indicating stem portion extending outside said metallic sphere to facilitate temperature reading.

15. A temperature measuring instrument according to claim 3, wherein said temperature sensing device is a mercury-in-glass thermometer having its bulb located within said metallic sphere and its indicating stem portion extending outside said metallic sphere to facilitate temperature reading.

16. A temperature measuring instrument according to claim 4, wherein said temperature sensing device is a mercury-in-glass thermometer having its bulb located within said metallic sphere and its indicating stem portion extending outside said metallic sphere to facilitate temperature reading.

17. A temperature measuring instrument according to claim 2, wherein said temperature sensing device is an electrical sensor device.

18. A temperature measuring instrument according to claim 3, wherein said temperature sensing device is an electrical sensor device.

19. A temperature measuring instrument according to claim 4, wherein said temperature sensing device is an electrical sensor device.

20. A temperature measuring instrument according to claim 2, wherein said temperature sensing device is an electronic sensor device.

21. A temperature measuring instrument according to claim 3, wherein said temperature sensing device is an electronic sensor device.

22. A temperature measuring instrument according to claim 4 wherein said temperature sensing device is an electronic sensor device.

* * * * *